(12) United States Patent
Kahlert et al.

(10) Patent No.: US 8,710,258 B2
(45) Date of Patent: Apr. 29, 2014

(54) STABILIZATION OF DICARBONATE DIESTERS WITH PROTONIC ACIDS

(71) Applicant: LANXESS Deutschland GmbH, Cologne (DE)

(72) Inventors: Steffen Kahlert, Leichlingen (DE); Johannes Kaulen, Odenthal (DE); Erasmus Vogl, Leverkusen (DE)

(73) Assignee: LANXESS Deutschland GmbH, Cologne, DE (US)

( * ) Notice: Subject to any disclaimer, the term of this patent is extended or adjusted under 35 U.S.C. 154(b) by 0 days.

(21) Appl. No.: 14/032,350

(22) Filed: Sep. 20, 2013

(65) Prior Publication Data

US 2014/0024850 A1  Jan. 23, 2014

Related U.S. Application Data

(62) Division of application No. 12/297,493, filed as application No. PCT/EP2007/003202 on Apr. 11, 2007, now Pat. No. 8,569,540.

(30) Foreign Application Priority Data

Apr. 22, 2006  (DE) .......................... 10 2006 018 845

(51) Int. Cl.
*C07C 67/48* (2006.01)

(52) U.S. Cl.
USPC .......................................................... 560/191

(58) Field of Classification Search
None
See application file for complete search history.

(56) References Cited

U.S. PATENT DOCUMENTS 4,565,648 A * 1/1986 Kopp et al. ................ 252/182.2

* cited by examiner

*Primary Examiner* — Johann R. Richter
*Assistant Examiner* — Jennifer C Sawyer
(74) *Attorney, Agent, or Firm* — Nicanor A. Kohncke

(57) ABSTRACT

By using protonic acids, diesters of dicarbonic acid may be stabilized against thermal and chemical decomposition over a relatively long period. Mixtures of diesters of dicarbonic acid and protonic acids are outstandingly suitable for preserving foods.

6 Claims, No Drawings

STABILIZATION OF DICARBONATE DIESTERS WITH PROTONIC ACIDS

This application is a divisional of pending U.S. patent application Ser. No. 12/297,493 filed Oct. 17, 2008, with the same title, which claims the right of priority under 35 U.S.C. §119 (a)-(d) and 35 U.S.C. §365 of International Application No. PCT/EP2007/003202, filed Apr. 12, 2007, which is entitled to the right of priority of German Patent Application No. 10 2006 018 845.4 filed Apr. 22, 2006, the contents of which are hereby incorporated by reference in their entirety The present invention relates to the use of protonic acids as stabilizers of diesters of dicarbonic acid, mixtures containing diesters of dicarbonic acid and protonic acids, and also the use of these mixtures for preserving foods, drinks and materials.

Diesters of dicarbonic acid are used, inter alia, for preserving foods, in particular drinks, as components of antimicrobial reagents, for deactivating enzymes in fermentation processes, or for the synthesis of fine chemicals or polymers. Diesters of dicarbonic acid are used, in addition, for example as catalysts for the oxidation of amines, or for synthesis, for example in the introduction of protecting groups.

It is known that the stability of diesters of dicarbonic acid can be relatively low at room temperature, and in particular at elevated temperature. In particular during purification, for example purification by distillation, or during relatively long storage, decomposition of diesters of dicarbonic acid can therefore occur. This decomposition can impair the quality and purity of the diesters of dicarbonic acid. In addition, the decomposition generally proceeds the more rapidly the more impurities are present. High purity and stabilization of diesters of dicarbonic acid are therefore highly desirable.

Methods for improving the thermal stability of diesters of dicarbonic acid are already known from the prior art. For instance, it is proposed, for example, to stabilize dialkyl dicarbonates by adding metal sulphates (cf. JP-A 48-4016). A disadvantage of this method, however, is that these metal sulphates are sparingly to poorly miscible with the dialkyl dicarbonates.

In addition, it is known to stabilize dialkyl dicarbonates by adding boron compounds (cf. JP-A 46-37810). However, a disadvantage in this case is the toxicity of the corresponding boron compounds. Usage in foods does not come into consideration for these additions.

In addition, carbonyl compounds and also heteroanalogous carbonyl compounds have been proposed as additives increasing the storage stability of solutions of dialkyl dicarbonates in solvents inert to dialkyl dicarbonates (cf. DE-A 3 231 397). However, solutions of dialkyl dicarbonates in customary aprotic solvents scarcely come into consideration as an addition to foods. In addition, stabilizing effects may only be achieved using relatively high percentage amounts of additions.

There was therefore a requirement for stabilizers which are suitable for protecting diesters of dicarbonic acid effectively against thermal breakdown.

Surprisingly, it has now been found that diesters of dicarbonic acid can be stabilized by addition of various protonic acids against thermal and/or chemical breakdown reactions such as can occur, for example in storage or purification by distillation.

The present invention therefore relates to the use of at least one protonic acid for stabilization of diesters of dicarbonic acid against chemical and/or thermal breakdown reactions.

The diesters of dicarbonic acid are preferably compounds of the general formula (I)

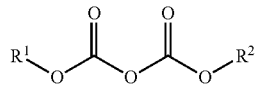

where
R$^1$ and R$^2$ independently of one another are straight-chain or branched C$_1$-C$_8$-alkyl, cycloalkyl, C$_2$-C$_8$-alkenyl, C$_1$-C$_8$-alkynyl or benzyl,
each of which is optionally monosubstituted to polysubstituted, identically or differently by halogen; nitro; cyano; C$_1$-C$_6$-alkoxy; dialkylamino; or are phenyl which is optionally monosubstituted to polysubstituted, identically or differently by halogen; nitro; cyano; alkyl; haloalkyl; alkoxy; haloalkoxy; acyl; acyloxy; alkoxycarbonyl; carboxyl,
preferably
R$^1$ and R$^2$ independently of one another are straight-chain or branched C$_1$-C$_8$-alkyl or C$_2$-C$_8$-alkenyl or benzyl,
particularly preferably
R$^1$ and R$^2$ independently of one another are straight-chain or branched C$_1$-C$_5$-alkyl or C$_3$-alkenyl or benzyl,
and very particularly preferably
R$^1$ and R$^2$ independently of one another are methyl, ethyl, isopropyl, tert-butyl, tert-amyl, allyl or benzyl.

The stabilizers of the invention are protonic acids of different acid strength.

Preferred protonic acids which come into consideration are, for example, the inorganic acids frequently used in industry and derivatives thereof, and also organic carboxylic acids and derivatives thereof.

Particularly preferred inorganic acids are hydrochloric acid, sulphuric acid, sulphurous acid, nitric acid, nitrous acid, hypochlorous acid, chlorous acid, chloric acid, perchloric acid and the like. The acids are customarily used as aqueous solutions.

Examples of derivatives of inorganic acids (sulphuric acid and sulphurous acid) which may be mentioned are particularly sulphonic acids, sulphinic acids and sulphamic acids. Particularly preferred derivatives from the group of the sulphonic acids are, for example, alkylsulphonic acids, phenylsulphonic acids, methylsulphonic acid, fluorosulphonic acid and strongly acidic ion exchangers as are disclosed, for example, by U.S. Pat. No. 6,646,017. Particularly preferred derivatives from the group of sulphamic acids are, for example, cyclohexanesulphamic acids.

Examples of organic carboxylic acids which may be mentioned are: saturated and monounsaturated or polyunsaturated aliphatic monocarboxylic acids, saturated and monounsaturated or polyunsaturated aliphatic dicarboxylic and polycarboxylic acids. Examples of derivatives of organic carboxylic acids which may be mentioned are: substitution products thereof such as hydroxycarboxylic acids, amino acids, aldehyde and keto acids, derivatives thereof such as carboxylic esters, carboxamides, carbonitriles and hydroxamic acids, and precursors thereof such as carbonyl halides, carboxylic anhydrides and ketenes.

Particularly preferred organic carboxylic acids are formic acid, acetic acid, propionic acid, butyric acid, valeric acid, caproic acid, heptanoic acid or longer-chain acids such as fatty acids. Likewise particular preference is given to those of the group of polycarboxylic acids, oxalic acid, malonic acid, succinic acid, maleic acid or glutaric acid and also derivatives thereof, for example monoesters thereof, such as methyl or ethyl esters. Likewise particular preference is given to those from the group of aliphatic monocarboxylic, dicarboxylic and polycarboxylic acid derivatives which additionally bear further OH groups on the carbon backbone and derivatives thereof, such as, for example citric acid, tartaric acid, malic acid, lactic acid or ascorbic acid. In this case the polycarboxylic acids can be present as partial alkyl esters and in addition the OH groups can be alkylated or likewise esterified. Also, further organic radicals can be bound via the OH functionalities to the carboxylic acids.

The said carboxylic acids can also be used in the form of their salts such as, for example, the sodium, potassium, magnesium or calcium salts.

If the abovementioned carboxylic acids have an asymmetric carbon atom, not only the pure enantiomers but also the enantiomeric or diastereomeric mixture may be used.

The protonic acids can be used as pure substances or as aqueous or alcoholic solutions. The compounds can equally be dissolved in advance in diesters of dicarbonic acid or other suitable solvents. The protonic acids can also be immobilized on surfaces.

In addition, of course, use can be made of the particular reactive precursors of the acids which in the presence of water hydrolyse, in situ, to give the abovementioned protonic acids. Examples of these are for instance acid chlorides or acid anhydrides.

The said stabilizers are generally used in an amount of 0.01 to 100 000 ppm, preferably in an amount of 0.1 to 10 000 ppm, particularly preferably in an amount of 0.1 to 3000 ppm, very particularly preferably in an amount of 0.1 to 2000 ppm, based on the diesters of dicarbonic acid or mixture thereof.

As a result of the use according to the invention, it is possible to stabilize diesters of dicarbonic acid in general against thermal and chemical breakdown reactions. Such breakdown reactions occur, for example, in storage.

The diesters of dicarbonic acid stabilized according to the invention are distinguished by improved storage stability. For instance, the diesters of dicarbonic acid stabilized in this manner can be stored for a plurality of months at room temperature without decomposition of the diesters of dicarbonic acid being observed.

The present invention further relates to mixtures containing one or more diesters of dicarbonic acid of the formula (I) illustrated above and one or more of the above generally and preferably described protonic acids generally in an amount of 0.01 to 100 000 ppm, preferably in an amount of 0.1 to 10 000 ppm, particularly preferably in an amount of 0.1 to 3000 ppm, very particularly preferably in an amount of 0.1 to 2000 ppm, based on the diesters of dicarbonic acid or mixture thereof.

Very particular preference is given to mixtures of at least one diester of dicarbonic acid of the formula (I), in particular dimethyl dicarbonate and/or diethyl dicarbonate with one or more protonic acids from the series of the inorganic acids described as preferred and particularly preferred, and derivatives thereof and the aliphatic monocarboxylic, dicarboxylic and polycarboxylic acids which additionally bear further OH groups on the carbon backbone, such as, for example, citric acid, tartaric acid, malic acid, lactic acid or ascorbic acid.

The inventive mixtures can be stored over a period of a plurality of months without decomposition of the diesters of dicarbonic acid present therein occurring.

The inventive mixtures are outstandingly suitable for preserving foods and in particular drinks against infection and/or decomposition by microorganisms, such as, for example, bacteria, fungi or yeasts.

The present invention likewise relates to the use of the inventive mixtures for preservation of foods and drinks.

The diesters of dicarbonic acid stabilized according to the invention are outstandingly suitable, for example, as cold disinfectants for still or carbonated drinks such as soft drinks, vitamin drinks, fruit juice drinks, tea drinks, alcoholic or dealcoholized wine drinks, fruit punches or some beers. Customarily, for this the diesters of dicarbonic acid are added in amounts between 10 and 250 ppm close in time to packaging the drinks. Admixture to the drinks is performed using special metering pumps. The diesters of dicarbonic acid act so as to control a series of microorganisms such as fermentative yeasts, moulds or fermentative bacteria. Examples which may be mentioned here are for instance *Saccharomyces cerevisiae, Mycoderma, Brettanomyces* spp, *Lactobacillus brevis, Lactobacillus buchneri* and many others.

Thermal breakdown reactions of diesters of dicarbonic acid also occur, furthermore, in particular in the purification, e.g. in the extraction or distillation of diesters of dicarbonic acid as carried out, for example, in the context of the production method for diesters of dicarbonic acid. By means of the inventive use of protonic acids it is possible to distil diesters of dicarbonic acid with relatively low losses and in relatively high purity.

The present invention therefore further relates to a method for the purification by distillation of diesters of dicarbonic acid, by admixing one or more diesters of dicarbonic acid of the above-specified formula (I) with one or more of the above generally preferably and particularly preferably mentioned protonic acids, generally in an amount of 0.01 to 100 000 ppm, preferably in an amount of 0.1 to 10 000 ppm, in each case based on the diesters of dicarbonic acid or mixture thereof, and subsequently distilling the mixture at a pressure of 5 to 100 mbar, preferably 10-50 mbar, and a temperature between 30 and 120° C., preferably between 40 and 90° C. Distillation columns customary in industry come into consideration for the distillation.

The yields of diesters of dicarbonic acid in the distillation are customarily >99%.

The present invention further relates to the stabilization of diesters of dicarbonic acid by setting an elevated, compared with high-purity diesters of dicarbonic acid, proton concentration to a pH of less than 6.5, preferably a pH of 6.0 to minus 5.0, and particularly preferably of 5.5 to 0. This can be achieved, for example, by the inventive addition of protonic acids in amounts from 0.01 to 100 000 ppm.

The proton concentration is measured in aqueous media customarily via the oxonium ions forming therein. As a conventional characteristic, therefore the pH is defined. The measurement of the pH can proceed, for example, after suitable sample preparation, via titration with suitable bases. The end point of the titration is indicated customarily via a colour change of an indicator dye. The pH can, however, also be measured, for example, by an electrochemical method. Here, customarily, use is made of pH electrodes, what are termed one-rod electrodes.

In organic liquids, depending on moisture content, likewise a pH can be measured, frequently very reproducibly, using pH electrodes. Another possibility, in the case of organic liquids, of measuring the proton concentration comprises a sample preparation. For example, in the case of diesters of dicarbonic acid, the proton concentration can be determined after extraction with ultrapure water. The diesters of dicarbonic acid are admixed as organic liquids with a sparing amount of water, well mixed, and the phases separated. From the pH of the aqueous phase, the amount of acid originally present in the diester of dicarbonic acid can be calculated.

The examples hereinafter serve to illustrate the subject matter of the present invention without, however, restricting it thereto.

EXAMPLES

Example 1

Corresponding to the data in Tables 1-4, in each case defined amounts of a defined high-purity diester of dicarbonic acid and the respectively stated additions were weighed in a 10 ml round-bottomed flask equipped with a magnetic stirrer. The exact amounts of the additions used in each case are likewise given in the tables.

The round-bottomed flask was tightly closed by a septum. In this septum was situated an orifice in which a Teflon tube was attached, which was passed into a vertical silicone-oil-filled 50 ml burette calibrated to 0.1 ml. On the scale of the burette, the amount of the carbon dioxide developing as a result of the decomposition of the diester of dicarbonic acid could be read off. The flask was promptly lowered into a constant temperature oil bath (stirred at 500 rpm) as specified in Tables 1-4 for the respective experiment. The depth of immersion of the flask was 2.0 cm.

After the respectively stated time, generally after 1, 2, 5, 10 and 15 minutes, the gas volume was read off. The gas volume is an index of the degree of decomposition of the diesters of dicarbonic acid to give $CO_2$. It thus inversely reflects the degree of stabilization by the additions tested.

In most cases the experiments were repeated in order to ensure reproducibility. Meaningful reproducibility was present in each case.

The results may be taken from the appended tables. High-purity diester of dicarbonic acid, in the observed time, released little carbon dioxide, but even contact with small amounts of silica gel, manganese dioxide or else only rough surfaces such as scratched glass drastically accelerated decomposition. Small amounts of the stabilizers were sufficient for effective reduction of the decomposition.

The fewer gaseous decomposition products diesters of dicarbonic acid release under temperature stress, the more favourably does distillation under vacuum proceed.

TABLE 1

| Dimethyl dicarbonate, 1670 ppm addition | | | | | | | |
|---|---|---|---|---|---|---|---|
| Temperature | 100 | 100 | 100 | 100 | 100 | 100 | 100 |
| Dimethyl dicarbonate Amount [g] | 3 | 3 | 3 | 3 | 3 | 3 | 3 |
| Addition Amount [mg] | without | silica gel 10 | silica gel 10 | silica gel 10 | silica gel 10 | silica gel 10 | silica gel 10 |
| Addition Amount in mg | without | without | water 5 | $H_2SO_4$ 5 | HCL 37.0% 5 | $HNO_3$ 65.0% 5 | perchloric acid 5 |
| Gas evolution [ml] | | | | | | | |
| Minute 1 | 0.1 | 1.0 | 2.4 | 0.1 | 0.6 | 0.5 | 0.2 |
| Minute 2 | 0.2 | 3.4 | 8.0 | 0.3 | 1.6 | 1.4 | 1.0 |
| Minute 5 | 0.6 | 20.3 | 26.8 | 1.9 | 30.0 | 2.5 | 10.9 |
| Minute 10 | 0.8 | 46.1 | 50.0 | 4.9 | 4.2 | 3.5 | 17.1 |
| Minute 15 | 1.3 | 50.0 | 50.0 | 10.2 | 6.1 | 4.5 | 23.1 |
| Temperature | 100 | 100 | 100 | 100 | 100 | 100 | 100 |
| Velcorin Amount [g] | 3 | 3 | 3 | 3 | 3 | 3 | 3 |
| Addition Amount [mg] | silica gel 10 | silica gel 10 | silica gel 10 | silica gel 10 | silica gel 10 | silica gel 10 | silica gel 10 |
| Addition | ascorbic acid | citric acid | L(−)malic acid | D(−)-tartaric acid 99% | L(+)-tartaric acid 99.5% p.a | N-cyclohexyl-sulphamic acid | acetic acid + $H_2SO_4$ |
| Amount in mg | 5 | 5 | 5 | 5 | 5 | 5 | 2.5 + 2.5 |
| Gas evolution [ml] | | | | | | | |
| Minute 1 | 0.5 | 0.6 | 0.1 | 1.0-0.5 | 0.2-0.3 | 0.2 | 0.1 |
| Minute 2 | 1.8 | 1.5 | 0.2 | 2.2-1.5 | 0.6-0.6 | 1.0 | 0.4 |
| Minute 5 | 8.2 | 2.5 | 0.4 | 3.3-2.6 | 0.9-1.1 | 9.6 | 1.5 |
| Minute 10 | 23.9 | 3.7 | 0.9 | 4.2-3.0 | 1.0-1.2 | 16.1 | 3.4 |
| Minute 15 | 33.6 | 6.4 | 2.7 | 4.7-3.7 | 1.1-1.5 | 19.6 | 6.4 |

| Dimethyl dicarbonate, 1670 ppm addition of stabilizer | | | | | | | |
|---|---|---|---|---|---|---|---|
| Temperature [° C.] | | | | | | | |
| | 100 | 100 | 100 | 100 | 100 | 100 | 100 |
| Dimethyl dicarbonate Amount [g] | | | | | | | |
| | 3 | 3 | 3 | 3 | 3 | 3 | 3 |
| Addition Amount [mg] | without | silica gel 10 | silica gel 10 | silica gel 10 | silica gel 10 | silica gel 10 | silica gel 10 |
| Addition of stabilizer | without | without | water | $H_2SO_4$ 98.0% | HCL 37.0% | $HNO_3$ 65.0% | perchloric acid |
| Amount [mg] | | | 5 | 5 | 5 | 5 | 5 |
| Gas evolution [ml] | | | | | | | |
| Minute 1 | 0.1 | 1.0 | 2.4 | 0.1 | 0.6 | 0.5 | 0.2 |
| Minute 2 | 0.2 | 3.4 | 8.0 | 0.3 | 1.6 | 1.4 | 1.0 |

-continued

| Dimethyl dicarbonate, 1670 ppm addition of stabilizer |
|---|

| | Temperature [° C.] | | | | | | |
|---|---|---|---|---|---|---|---|
| | 100 | 100 | 100 | 100 | 100 | 100 | 100 |
| | Dimethyl dicarbonate Amount [g] | | | | | | |
| | 3 | 3 | 3 | 3 | 3 | 3 | 3 |
| Minute 5 | 0.6 | 20.3 | 26.8 | 1.9 | 3.0 | 2.5 | 10.9 |
| Minute 10 | 0.8 | 46.1 | 50.0 | 4.9 | 4.2 | 3.5 | 17.1 |
| Minute 15 | 1.3 | 50.0 | 50.0 | 10.2 | 6.1 | 4.5 | 23.1 |
| Addition | silica gel | silica gel | silica gel | silica gel | silica gel | silica gel | silica gel |
| Amount [mg] | 10 | 10 | 10 | 10 | 10 | 10 | 10 |
| Addition of stabilizer | ascorbic acid | citric acid | L(−)-malic acid | D(−)-tartaric acid 99%. | L(+)-tartaric acid 99.5% p.a. | N-cyclohexyl-sulphamic acid | acetic acid + H$_2$SO$_4$ 98% |
| Amount [mg] | 5 | 5 | 5 | 5 | 5 | 5 | 2.5 + 2.5 |
| Gas evolution [ml] | | | | | | | |
| Minute 1 | 0.5 | 0.6 | 0.1 | 1.0 | 0.2 | 0.2 | 0.1 |
| Minute 2 | 1.8 | 1.5 | 0.2 | 2.2 | 0.6 | 1.0 | 0.4 |
| Minute 5 | 8.2 | 2.5 | 0.4 | 3.3 | 0.9 | 9.6 | 1.5 |
| Minute 10 | 23.9 | 3.7 | 0.9 | 4.2 | 1.0 | 16.1 | 3.4 |
| Minute 15 | 33.6 | 6.4 | 2.7 | 4.7 | 1.1 | 19.6 | 6.4 |

| Temperature [° C.] | 100 | 100 | 100 |
|---|---|---|---|
| Dimethyl dicarbonate Amount [g] | 3 | 3 | 3 |
| Addition | silica gel | silica gel | silica gel |
| Amount [mg] | 10 | 10 | 10 |
| Addition of stabilizer | benzene-sulphonic acid | toluene-sulphonic acid | methane-sulphonic acid |
| Amount [mg] | 5 | 5 | 5 |
| Gas evolution [ml] | | | |
| Minute 1 | 0.5 | 0.7 | 0.6 |
| Minute 2 | 1.4 | 1.6 | 1.1 |
| Minute 5 | 2.5 | 2.6 | 2.0 |
| Minute 10 | 3.8 | 4.1 | 2.4 |
| Minute 15 | 6.0 | 5.3 | 3.2 |

TABLE 3

| Dimethyl dicarbonate, 1670 ppm addition of stabilizer | | | |
|---|---|---|---|
| Temperature [° C.] | 100 | 100 | 100 |
| Dimethyl dicarbonate Amount [g] | 3 | 3 | 3 |
| Addition | without | surface of the flask highly internally scratched | surface of the flask highly internally scratched |
| Addition of stabilizer | without | without | L(+)-tartaric acid |
| Amount [mg] | | | 5 |
| Gas evolution [ml] | | | |
| Minute 1 | 0.1 | 0.7 | 0.6 |
| Minute 2 | 0.2 | 1.3 | 1.4 |
| Minute 5 | 0.5 | 2.2 | 2.1 |
| Minute 10 | 1.3 | 3.8 | 2.7 |
| Minute 15 | 2.7 | 5.7 | 3.0 |

TABLE 2

| Dimethyl dicarbonate, 1670 ppm addition of stabilizer | | | | | | | |
|---|---|---|---|---|---|---|---|
| Temperature [° C.] | 100 | 100 | 100 | 100 | 100 | 100 | 100 |
| Dimethyl dicarbonate Amount [g] | 3 | 3 | 3 | 3 | 3 | 3 | 3 |
| Addition | Manganese dioxide | Manganese dioxide | Manganese dioxide | Manganese dioxide | Manganese dioxide | Manganese dioxide | Manganese dioxide |
| Amount [mg] | 10 | 10 | 10 | 10 | 10 | 10 | 10 |
| Addition of stabilizer | without | HCl 37.0% | HNO$_3$ 65.0% | citric acid | L(−)-malic acid | L(+)-tartaric acid 99.5% p.a. | water |
| Amount [mg] | | 5 | 5 | 5 | 5 | 5 | 5 |
| Gas evolution [ml] | | | | | | | |
| Minute 1 | 3.8 | 0.9 | 0.9 | 2.5 | 0.5 | 2.9 | 7.1 |
| Minute 2 | 9.3 | 2.0 | 2.8 | 5.9 | 1.2 | 6.2 | 26.4 |
| Minute 5 | 21.7 | 6.9 | 7.4 | 8.8 | 2.7 | 9.0 | 35.4 |
| Minute 10 | 31.1 | 9.6 | 13.6 | 11.7 | 3.9 | 10.5 | 46.1 |
| Minute 15 | 41.5 | 12.2 | 19.6 | 15.9 | 5.3 | 11.2 | 50.0 |

TABLE 4

| Dimethyl dicarbonate, <1000 ppm addition of stabilizer | | | | | |
|---|---|---|---|---|---|
| Temperature [° C.] | 100 | 100 | 100 | 100 | 100 |
| Dimethyl dicarbonate Amount [g] | 3 | 3 | 3 | 3 | 3 |
| Addition | silica gel | silica gel | silica gel | silica gel | silica gel |
| Amount [mg] | 10 | 10 | 10 | 10 | 10 |
| Addition of stabilizer | 100 ppm malic acid | 10 ppm $H_2SO_4$ 98.0% | 100 ppm $H_2SO_4$ 98.0% | 100 ppm L(+)-tartaric acid | 100 ppm $HNO_3$ 65.0% |
| Gas evolution [ml] | | | | | |
| Minute 1 | 0.2 | 0.7 | 0.9 | 0.4 | 0.2 |
| Minute 2 | 1.4 | 1.9 | 1.5 | 1.7 | 0.6 |
| Minute 5 | 14.3 | 11.2 | 2.7 | 16.1 | 2.5 |
| Minute 10 | 40.4 | 33.5 | 4.2 | 38.7 | 34.4 |
| Minute 15 | | | 15.5 | | |

Example 2

The association between stabilization and the pH determined directly by a pH electrode was measured experimentally. High-purity dimethyl dicarbonate was first admixed with different amounts of acid or base. The pH then established was measured directly using a pH electrode (one-rod electrode) from Mettler Toledo, Model Inlab 1010. The electrode was calibrated in advance in buffer solutions. Thereupon the instability was determined experimentally as a function of pH in a similar manner to the procedure in Example 1. The respective values for carbon dioxide evolution may be found in the table. A clear correlation can be seen between proton content and stability. Likewise, the amount of inorganic acid present in the diester of dicarbonic acid after extraction with ultrapure water was determined. For this the dimethyl dicarbonate was extracted with a sparing amount of high-purity water and the pH measured in this water using the glass electrode before or after phase separation. Thereafter the pH was converted to the original dicarbonate volume. This procedure gave identical values and less drift of the pH electrode. The solutions were flushed with argon during the pH determination in order to prevent the pH from being influenced by carbon dioxide.

| Dimethyl dicarbonate, pH dependence | | | | | | | | | | |
|---|---|---|---|---|---|---|---|---|---|---|
| Temperature [° C.] | | | | | | | | | | |
| | 100 | 100 | 100 | 100 | 100 | 100 | 100 | 100 | 100 | 100 |
| Dimethyl dicarbonate Amount [g] | | | | | | | | | | |
| | 3 | 3 | 3 | 3 | 3 | 3 | 3 | 3 | 3 | 3 |
| Addition | silica gel 1 | silica gel 1 | silica gel 1 | silica gel 1 | silica gel 1 | silica gel 1 | silica gel 1 | silica gel 1 | silica gel 1 | silica gel 1 |
| Amount [mg] | 10 | 10 | 10 | 10 | 10 | 10 | 10 | 10 | 10 | 10 |
| Measured pH | −1 | 0.6 | 2.6 | 3.9 | 4.2 | 5.9 | 6.3 | 7.9 | 8.4 | 9.5 |
| Gas evolution [ml] | | | | | | | | | | |
| Minute 1 | 0.3 | 0.1 | 1.1 | 0.3 | 0.7 | 0.4 | 1.0 | 1.9 | 3.3 | 6.4 |
| Minute 2 | 0.6 | 0.2 | 2.2 | 1.2 | 1.9 | 1.8 | 7.8 | 18.2 | 30.9 | 42.5 |
| Minute 5 | 1.0 | 1.0 | 5.3 | 5.6 | 13.4 | 13.3 | 29.6 | 49.2 | 50.0 | 50.0 |
| Minute 10 | 1.4 | 1.9 | 8.2 | 22.2 | 37.3 | 37.2 | 50.0 | 50.0 | 50.0 | 50.0 |
| Minute 15 | 1.8 | 3.3 | 10.9 | 35.2 | 50.0 | 50.0 | 50.0 | 50.0 | 50.0 | 50.0 |

What is claimed is:

1. A process for stabilization of diesters of dicarbonic acid against chemical and thermal breakdown reactions, comprising:
   admixing said diesters of dicarbonic acid with at least one protonic acid, wherein the protonic acid is selected from the group of an inorganic acid and derivatives thereof and an organic carboxylic acid, and
   further wherein said organic carboxylic acid is selected from the group consisting of saturated and monounsaturated or polyunsaturated aliphatic monocarboxylic acids, saturated and monounsaturated or polyunsaturated aliphatic dicarboxylic and polycarboxylic acids and derivatives thereof, hydroxamic acids, hydroxycarboxylic acids, amino acids, and keto acids, and
   wherein the diesters of dicarbonic acid is a compound of the general formula (I)

$$R^1\text{O}-\underset{\text{O}}{\overset{\text{O}}{\text{C}}}-\text{O}-\underset{\text{O}}{\overset{\text{O}}{\text{C}}}-\text{O}R^2 \quad (I)$$

where
   $R^1$ and $R^2$ independently of one another are straight-chain or branched $C_1$-$C_8$-alkyl, cycloalkyl, $C_2$-$C_8$-alkenyl, $C_2$-$C_8$-alkynyl or benzyl, each of which is optionally monosubstituted to polysubstituted, identically or differently by halogen; nitro; cyano; $C_1$-$C_6$-alkoxy; dialkylamino; or are phenyl which is optionally monosubstituted to polysubstituted, identically or differently by halogen; nitro; cyano; alkyl; haloalkyl; alkoxy; haloalkoxy; acyl; acyloxy; alkoxycarbonyl; carboxyl.

2. The process according to claim 1, wherein the inorganic acid is selected from the group consisting of hydrochloric acid, sulphuric acid, sulphurous acid, nitric acid, nitrous acid, hypochlorous acid, chlorous acid, chloric acid, perchloric acid, and mixtures thereof.

3. The process according to claim 1, wherein the derivatives of the inorganic acids are selected from the group consisting of alkylsulphonic acids, phenylsulphonic acids, methylsulphonic acid, fluorosulphonic acid, and strongly acidic ion exchangers.

4. The process according to claim 1 wherein the diesters of dicarbonic acid are dimethyl dicarbonate or diethyl dicarbonate.

5. The process according to claim 1, wherein the protonic acid is used in an amount of 0.01 to 100 000 ppm, based on diesters of dicarbonic acid.

6. The process according to claim 1, wherein the stabilization of diesters of dicarbonic acid against chemical and thermal breakdown reactions is during workup, extraction, distillation or storage steps of such reactions.

* * * * *